US006647985B1

United States Patent
Prywes

(12) United States Patent
(10) Patent No.: US 6,647,985 B1
(45) Date of Patent: Nov. 18, 2003

(54) BARRIER SURGICAL DRAPE FOR SPECULUMS OR RETRACTORS

(76) Inventor: Arnold S. Prywes, 12 Jason Ct., Dix Hills, NY (US) 11746

( * ) Notice: Subject to any disclaimer, the term of this patent is extended or adjusted under 35 U.S.C. 154(b) by 0 days.

(21) Appl. No.: 09/694,102

(22) Filed: Oct. 20, 2000

Related U.S. Application Data

(60) Provisional application No. 60/160,796, filed on Oct. 21, 1999.

(51) Int. Cl.$^7$ ............................................... A61B 19/08
(52) U.S. Cl. ....................... 128/853; 128/849; 128/854
(58) Field of Search ................... 128/849–856, 128/857; 602/52, 54, 57, 58; 428/40.1, 192, 41.7, 41.8, 42.2, 121

(56) References Cited

U.S. PATENT DOCUMENTS

| | | | |
|---|---|---|---|
| 3,698,395 A | * 10/1972 | Hasson | ........................ 606/218 |
| 3,916,887 A | * 11/1975 | Kelly | ......................... 128/851 |
| 4,323,062 A | * 4/1982 | Canty | |
| 4,412,532 A | * 11/1983 | Anthony | |
| 5,213,114 A | * 5/1993 | Bailey, Jr. | |
| 5,409,018 A | * 4/1995 | Mills | ........................... 128/852 |
| 5,515,868 A | * 5/1996 | Mills | ........................... 128/854 |
| 5,649,550 A | * 7/1997 | Crook | |

* cited by examiner

Primary Examiner—Nicholas D. Lucchesi
Assistant Examiner—Lalita M. Hamilton
(74) Attorney, Agent, or Firm—Ladas & Parry

(57) ABSTRACT

A speculum drape is provided which is adapted for attachment to a surgical speculum or retractor to preserve a sterile field at a surgical site. The speculum drape is made of a sheet of surgical drape material having an opening of a size corresponding to a surgical site in which a surgical operation is to be performed. The drape material has a plurality of tabs, flaps or other constructions by which the drape material can be secured to the surgical speculum or retractor. The tabs may be provided with adhesive material on one surface for securing the tabs to the speculum or retractor and with adhesive material on the other surface for being secured to underlying tissue of a patient or a conventional surgical drape placed on the patient.

18 Claims, 4 Drawing Sheets

BARRIER SURGICAL DRAPE FOR SPECULUMS OR RETRACTORS

This application claims benefit of application Ser. No. 60/160,796 filed Oct. 21, 1999.

FIELD OF THE INVENTION

The invention relates to a barrier surgical drape for use with a speculum or retractor in the performance of surgery. The drape is denoted hereafter as a speculum or retractor drape.

The drape of the invention is applicable to the performance of surgery by attaching or adhering the drape to the retractor or speculum. It thereby produces a watertight seal to the speculum and to the surrounding tissue. The drape can be used in a number of surgical procedures such as in ocular surgery with an eyelid speculum, in gynecologic, or obstetrical surgery by attachment to a vaginal speculum, in laporoscopic or endoscopic surgery, otologic or laryngologic surgery, nasal surgery, orthopedic or neurosurgery, to provide a sterile field throughout the performance of the surgical procedure.

BACKGROUND

Surgical procedures are typically performed after the tissue is cleansed with antiseptic solutions and draped with sterile drapes of cloth or plastic material. Typically the plastic material is adherent to the tissues to act as a barrier to contamination of the surgical site. The drape usually has an opening for incising the exposed tissue and for manipulation of the tissues within this opening. After the entry into the tissues the use of fluid, suction or wiping during the surgical procedure often results in disruption of the adhesion of the drape to the external tissues. When a speculum or retractor is used to hold tissues away from the surgical field, no barrier between the speculum and the surgical site exists when the drape loses its adhesion. Often the drape may bunch together and obscure the view of the surgeon. The lack of adhesion may result in bacterial entry into the surgical wound, possibly causing infection. In ocular surgery the lid retractors or speculums will often not hold the eyelashes away from the surgical site thereby impeding the performance of the procedures.

Plastic drapes from different manufacturers have varying degrees of adhesion to underlying tissue surfaces and their loss of adhesion causes the sterile drape surrounding the surgical site often to loosen from the underlying tissues and impede the movement of the surgical instruments by obstructing the path to the surgical site. The result of these difficulties with surgical draping produces increased difficulty in performing the surgery, increased time wasted in adjusting the drape resulting in prolonged operative and anesthesia times, placing patients in longer procedures.

SUMMARY OF THE INVENTION

It is an object of the invention to provide a barrier drape which attaches to or is integral with surgical speculums or retractors to minimize the problems associated with present surgical drapes as described above.

A particular object of the invention is to provide such a drape which is adapted for speculums or retractors used during a surgical procedure.

A feature of the invention is to provide a drape which is specially adapted to attach directly to the retractor or speculum, and which may also be attached to an underlying surgical drape which is adhered to the area surrounding a surgical field.

According to the invention, a speculum drape is provided which comprises a sheet of drape material having attachment means, such as, tabs having adhesive on one surface enabling attachment of the drape to a surgical speculum or retractor, and adhesive on the other surface for attaching the drape to surrounding tissue or to a surgical drape underneath the speculum drape.

In further accordance with the invention, when the retractor or speculum is to be used only once, the speculum drape can be integral with the speculum or retractor such that the barrier function of the drape is contiguous with the speculum or retractor.

In further accordance with the invention, the speculum drape may have channeling devices, such as wicks, tubes or pockets to divert irrigation or bodily fluids from the surgical site thereby keeping the surgical site dry, and allowing for improved visualization of the surgical site by the surgeon.

In further accordance with the invention, the speculum drape prevents the intrusion of the eyelashes in eye surgery thereby stopping the unwanted lashes from obscuring or interfering with the surgery.

In further accordance with the invention, the speculum drape provides sterility by adhering directly to the area surrounding the surgical site and to the speculum.

DETAILED DESCRIPTION

Figure 1:
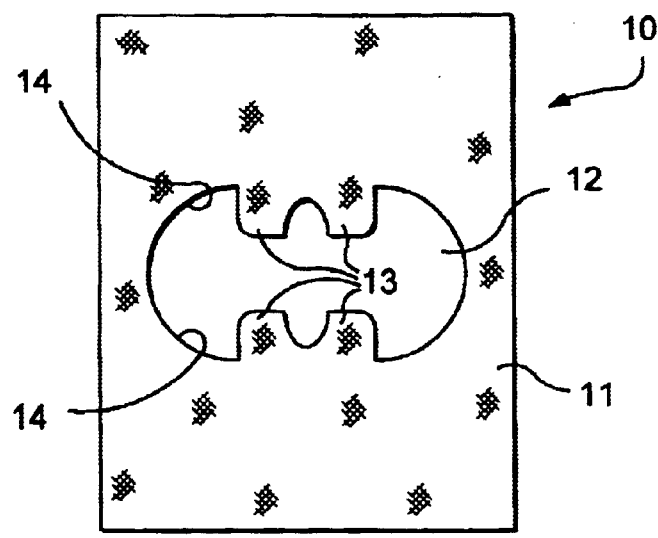
FIG. 1 is a plan view of a speculum drape according to the invention.

FIG. 1 shows a speculum drape 10 which is comprised of a sheet of surgical drape material 11 of rectangular outline. The surgical drape material can be made of cloth or plastic as well known in the art. The drape 10 has an opening 12 of a size to expose a surgical site of a patient at which a surgical operation is to be performed. The drape 10 is provided with a plurality of tabs 13 extending from opposite edges 14 of the opening 12 towards one another for a purpose to be explained subsequently. The tabs 13 can be formed by making a U-shaped cut-out in a projecting flap extending from an edge 14.

Figure 2:
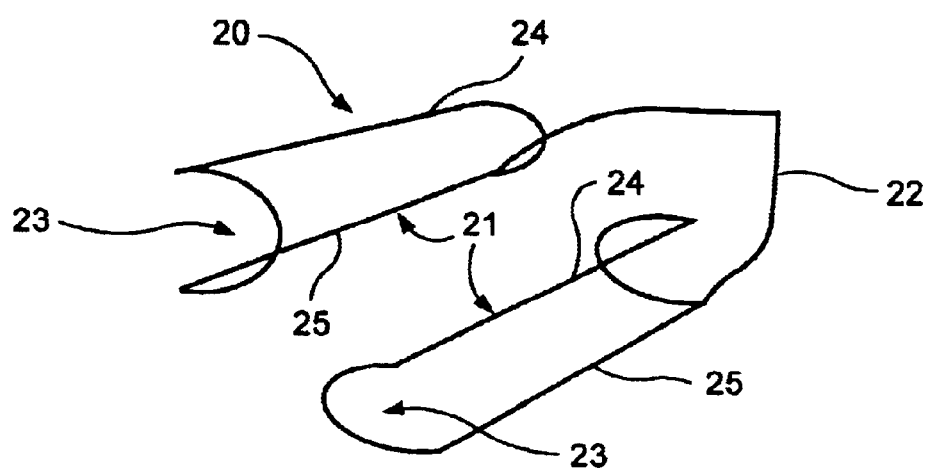
FIG. 2 is a perspective view of a conventional surgical speculum or retractor with which the speculum drape is adapted to cooperate.

FIG. 2 shows a conventional speculum or retractor 20 adapted to engage opposite edges of incised tissue of a patient to hold the edges away from another and enable the surgeon to operate at the surgical site. The speculum can also hold open the edges of a part of the body on which surgery is to be performed without an incision, for example, the eyelid of a patient. The retractor is made of a resilient material, such as a wire. In the course of an operation in which a surgical drape is used, the drape can become bunched up or displaced away from the retractor and can interfere with the operation or no longer provide the antiseptic protection for the surrounding tissue of the body.

Figure 3:
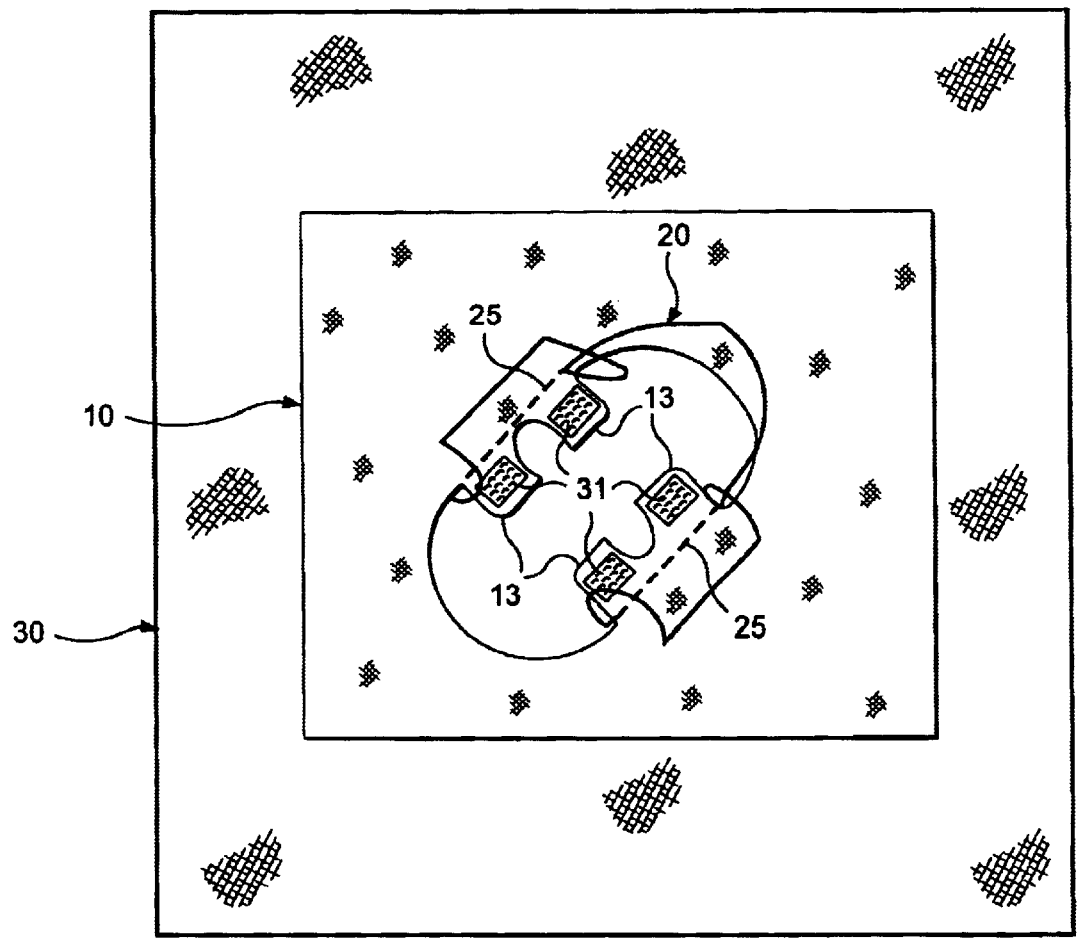
FIG. 3 shows the retractor and the speculum drape in a first stage of assembly.

The resilient wire of the speculum or retractor 20 is formed with two opposite retainer portions 21 which are joined by a connection portion 22 to provide lateral resiliency by which the retainer portions 21 can be urged towards and away from one another. The retainer portions 21 are bent to a U-shape to define openings 23 into which the edges of the tissue to be separated can be inserted. The retainer portions 21 each have upper legs 24 and lower legs 25. The edges of the tissue are received in openings 23 while the retainer portions 21 are pressed towards one another so that when the retainer portions are released the tissue edges are kept away from one another. The surgical drape which can lie beneath the speculum or retractor is shown in FIG. 3 by numeral 30.

In normal use, when a surgical incision is to be made the patient is covered with surgical drape 30 and the speculum 20 is applied after the incision has been made. When no incision is made, for example, in eye surgery, the speculum is used without a surgical drape.

In accordance with the invention, the speculum 20 is associated with a speculum drape for all surgical procedures to avoid the problems previously described.

Figure 4:
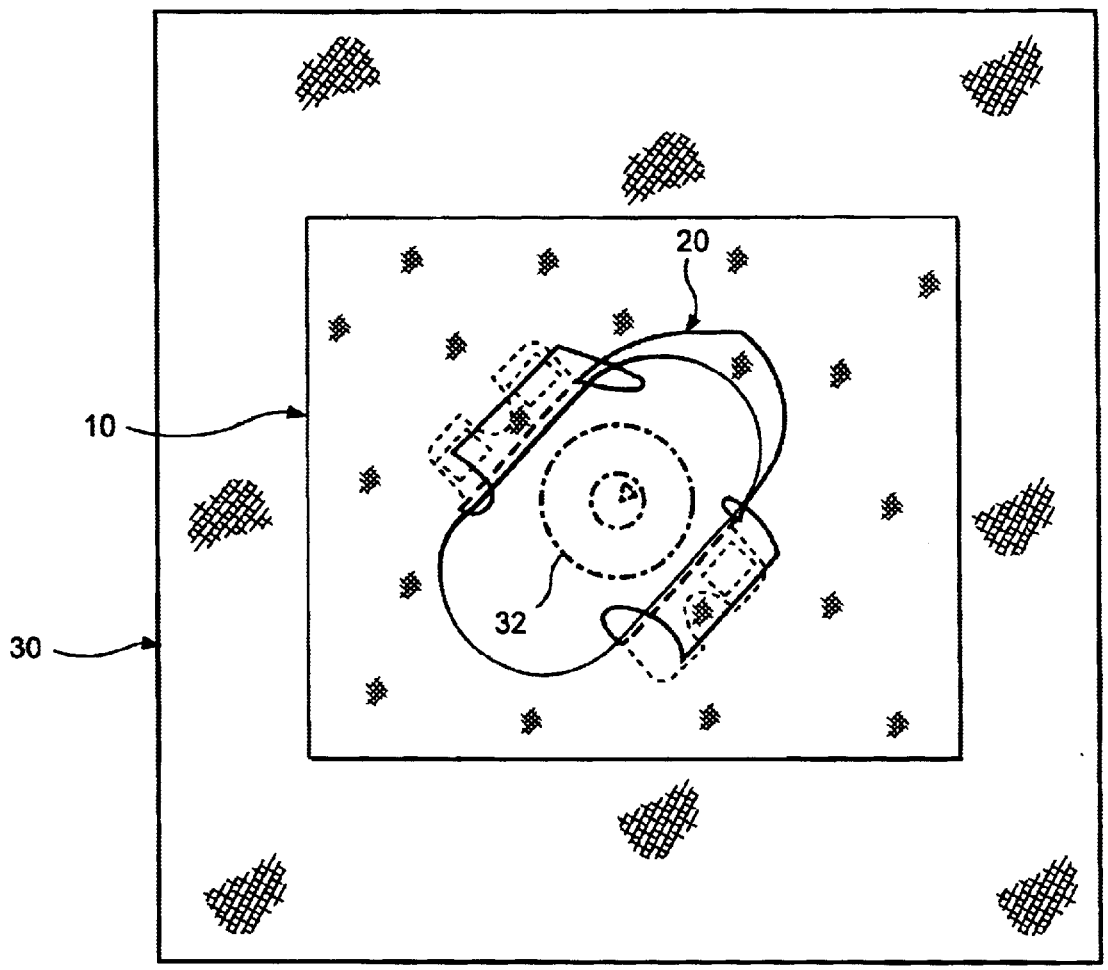
FIG. 4 shows the retractor and speculum drape in a completed stage of assembly for use in optical surgery.

The speculum drape 10 is generally of smaller size than the surgical drape 30. The speculum drape 10 is attached to the speculum 20 so that its opening 12 will provide access to the surgical site. In order to attach the speculum drape 10 to the speculum 20, the tabs 13 are fitted over lower legs 25 of the retainer portions as shown in FIG. 3. The lower faces of the tabs 13 are provided with securing means 31 such that when the tabs 13 are folded over the lower legs 25 of the retainer portions, the securing means can secure the tabs to the back face of the speculum drape whereby the speculum drape 10 will now be secured to the speculum as shown in FIG. 4. Thereby, the subject of an operation (an eye 32 in FIG. 4), will be exposed and the surrounding lid tissue will be covered by the drape material of the speculun drape. When the speculum is used with an underlying surgical drape 30, even if the drape 30 should shift, the speculum drape 10 will provide antiseptic conditions. The securing means 31 can be in the form of an adhesive material or a snap connection or a connection made of releasable interlocking barbs and loops sold under the trademark VELCRO. If the speculum or retractor is to be used once and then disposed of, the speculum and the speculum drape can be permanently and integrally secured together.

Figure 5:
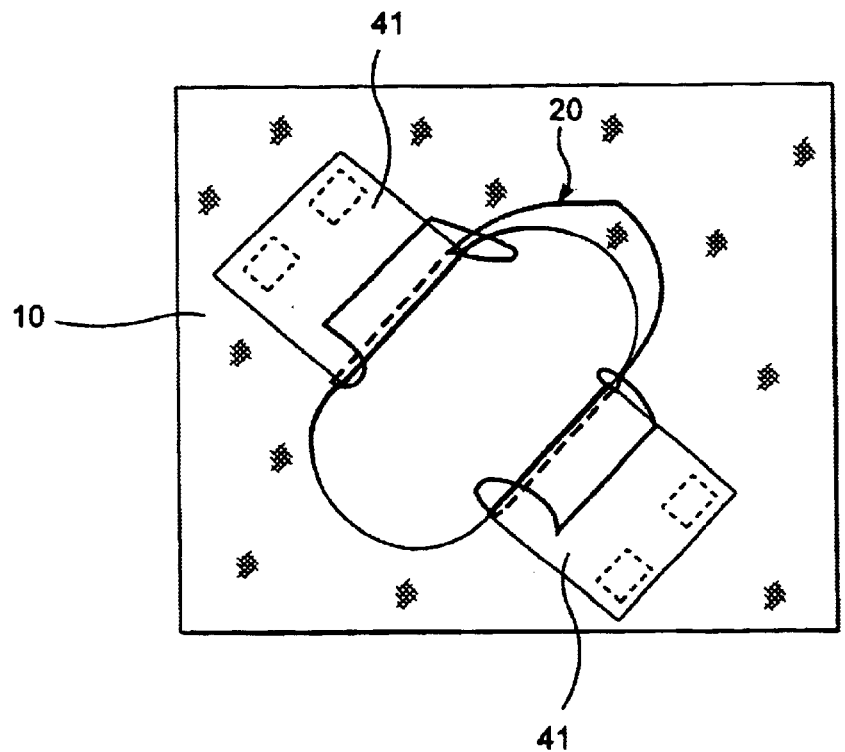
FIG. 5 shows a modification of the speculum drape in FIG. 4.
Figure 6:
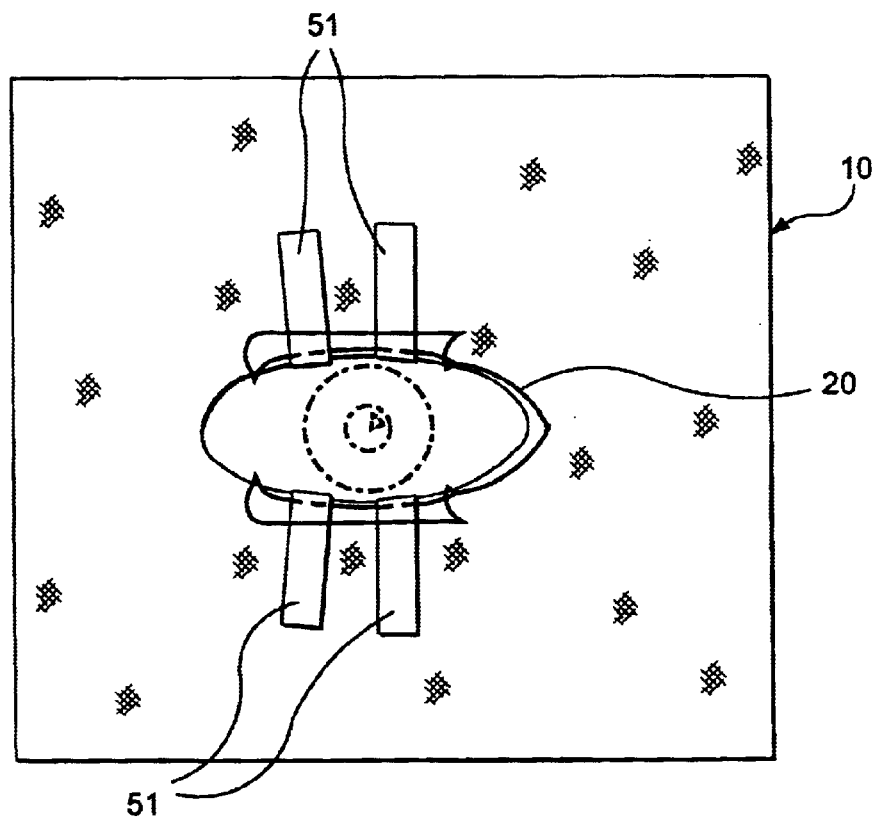
FIG. 6 shows another modified speculum drape.

Instead of forming the tabs 13 as individual projecting elements, the tabs can be formed as an elongate flap 41, as shown in FIG. 5. In FIG. 6, the tabs 51 are substantially elongated elements. The tabs 13, flap 41 and the tabs 51 can be provided with adhesive on their upper surfaces so that the speculum drape can be secured to an underlying surgical drape or directly to the tissue when no surgical drape is used.

Although the invention is disclosed with reference to particular embodiments thereof, it will become apparent to those skilled in the art that numerous modifications and variations can be made which will fall within the scope and spirit of the invention as defined by the attached claims.

What is claimed:

1. A speculum drape adapted for attachment to a surgical speculum or retractor which is used in ophthalmic procedures, said speculum or retractor being made of elastic material to resiliently hold open an eyelid of a patient, said speculum drape comprising a sheet of surgical drape material having an opening of a size corresponding to a site in the eye of a patient at which an ophthalmic procedure is to be performed, said drape material having an attachment means for attaching said drape material to the elastic surgical speculum or retractor so that the opening in the surgical drape material is positioned at said site, said drape material having an extent to cover and hold down eyelashes of the eye of the patient, said attachment means comprising a plurality of projecting tabs on said sheet of drape material for engaging said speculum or retractor to be secured therewith, said projecting tabs being of a length to wrap around a portion of said speculum or retractor to secure the drape thereto, and securing means on a surface of said tabs for securing said tabs to a back surface of the sheet of drape material after the tabs have been wrapped around the portion of the speculum or retractor, wherein said securing means comprises a hook and loop connection.

2. A speculum drape adapted for attachment to a surgical speculum or retractor which is used in ophthalmic procedures, said speculum or retractor being made of elastic material to resiliently hold open an eyelid of a patient, said speculum drape comprising a sheet of surgical drape material having an opening of a size corresponding to a site in the eye of a patient at which an ophthalmic procedure is to be performed, said drape material having an attachment means for attaching said drape material to the elastic surgical speculum or retractor so that the opening in the surgical drape material is positioned at said site, said drape material having an extent to cover and hold down eyelashes of the eye of the patient, said attachment means comprising a plurality of projecting tabs on said sheet of drape material for engaging said speculum or retractor to be secured therewith, said projecting tabs being of a length to wrap around a portion of said speculum or retractor to secure the drape thereto, and securing means on a surface of said tabs for securing said tabs to a back surface of the sheet of drape material after the tabs have been wrapped around the portion of the speculum or retractor, wherein said securing means comprises a snap connection.

3. A speculum drape adapted for attachment to a surgical speculum or retractor for use at a surgical site, said speculum drape comprising a sheet of surgical drape material having an opening of a size corresponding to a surgical site at which a surgical operation is to be performed, said drape material having an attachment means for attaching said drape material to the surgical speculum or retractor, said attachment means comprising a plurality of projecting tabs on said sheet of drape material for engaging said speculum or retractor to be secured therewith, said tabs being of a length to wrap around a portion of said speculum or retractor to secure the drape thereto, and securing means on a surface of said tabs for securing said tabs to a back surface of the sheet of drape material after the tabs have been wrapped around the portion of the speculum or retractor and an adhesive material on a front surface of said tabs for securing said tabs and thereby said sheet of drape material to a surface under the drape material.

4. The speculum drape as claimed in claim 3, wherein said adhesive material on said front surface of said tabs is adapted for attachment to a separate surgical drape.

5. The speculum drape as claimed in claim 4, wherein said sheet of drape material of the speculum drape has an extent which is less than the extent of the separate surgical drape.

6. The speculum drape as claimed in claim 3, wherein said adhesive material on said opposite surface of said tabs is adapted for attachment to human tissue.

7. The speculum drape as claimed in claim 3, wherein said speculum drape is made of cloth or plastic material.

8. A speculum drape adapted for attachment to a surgical speculum or retractor for use at a surgical site, said speculum drape comprising a sheet of surgical drape material having an opening of a size corresponding to a surgical site at which a surgical operation is to be performed, said drape material having an attachment means for attaching said drape material to the surgical speculum or retractor, said attachment means comprising a plurality of flexible projecting tabs on said sheet of drape material for wrapping around said speculum or retractor to be secured therewith, said opening in said sheet of drape material having opposite edges and said tabs are connected to said opposite edges and extend in said opening towards one another.

9. The speculum drape as claimed in claim 8, wherein said speculum drape is made of cloth or plastic material.

10. The speculum drape as claimed in claim 8, wherein two of said tabs are located at each of said opposite edges.

11. The speculum drape as claimed in claim 8, wherein said tabs are formed by a U-shaped cut-out in a projecting flap extending from said sheet of drape material.

12. The speculum drape as claimed in claim 8, wherein said tabs are in the form of flaps which extend along a substantial length of said opening.

13. An article adapted for use in an ophthalmic procedure comprising the combination of a speculum or retractor and a surgical drape having means for affixing the drape to the speculum or refractor, said speculum or refractor being configured to engage and hold apart opposite edges of an eyelid of a patient to expose the eye of the patient, said surgical drape being made of a thin sheet of flexible material and having an opening therein to expose the eye for the ophthalmic procedure and being of an extent to cover and hold down the eyelid and eyelashes of the patient, said speculum or retractor including opposite retainer portions which resiliently hold apart the edges of the eyelids, said drape being affixed by said means to said retainer portions, wherein said means for affixing the drape to the speculum or retractor detachably connects the drape to the speculum or retractor.

14. The article as claimed in claim 13, wherein said means for affixing the drape to the speculum or retractor comprises a plurality of projecting tabs on said sheet of drape material for engaging said speculum or retractor to be secured therewith wherein said tabs are formed by a U-shaped cut-out in a projecting flap extending from said sheet of drape material.

15. The speculum drape as claimed in claim 13, wherein said means for affixing the drape to the speculum or retractor comprises a plurality of projecting tabs on said sheet of drape material for engaging said speculum or retractor to be secured therewith wherein said tabs are in the form of flaps which extend along a substantial length of said opening.

16. The article of claim 13, wherein said speculum or retractor is made of resilient material.

17. The article of claim 13, wherein said speculum or retractor comprises a resilient wire.

18. The speculum drape as claimed in claim 8, wherein said sheet of drape material and said speculum or retractor are secured together by said attachment means permanently as an integral assembly adapted for a single use.

* * * * *